United States Patent [19]

Delente et al.

[11] Patent Number: 5,151,347
[45] Date of Patent: Sep. 29, 1992

[54] CLOSED PHOTOBIOREACTOR AND METHOD OF USE

[75] Inventors: Jacques J. Delente, Kensington; Paul W. Behrens, Ellicott City; Scot D. Hoeksema, Elkridge, all of Md.

[73] Assignee: Martek Corporation, Columbia, Md.

[21] Appl. No.: 441,553

[22] Filed: Nov. 27, 1989

[51] Int. Cl.$^5$ .................... C12N 1/12; C12Q 3/00; C12M 1/34
[52] U.S. Cl. .................... 435/3; 435/168; 435/243; 435/257; 435/284; 435/289; 435/311; 435/313; 435/315; 435/813; 47/1.4
[58] Field of Search ............. 435/281, 300, 284–286, 435/3, 173, 168, 257, 287, 289, 311, 313, 315, 813, 801, 314, 316, 243; 423/219; 47/1.4

[56] References Cited

U.S. PATENT DOCUMENTS

| | | | |
|---|---|---|---|
| 2,144,497 | 1/1939 | Pelle | 423/219 |
| 2,815,607 | 12/1957 | Schroeder | . |
| 3,361,531 | 1/1968 | Erb et al. | 423/219 |
| 3,849,539 | 11/1974 | Coleman | 423/219 |
| 3,852,406 | 12/1974 | Krauss et al. | 423/219 |
| 3,854,240 | 12/1974 | Oldham et al. | 47/1.4 |
| 3,986,297 | 10/1976 | Ichimura et al. | 47/1.4 |
| 4,084,346 | 4/1978 | Stengel et al. | 435/315 |
| 4,119,706 | 10/1978 | Rogers | 423/219 |
| 4,192,773 | 3/1980 | Yoshikawa et al. | 423/219 |
| 4,473,970 | 10/1984 | Hills | 47/1.4 |
| 4,477,418 | 10/1984 | Mullhaupt et al. | 423/219 |
| 4,868,123 | 9/1989 | Berson et al. | 435/290 |

FOREIGN PATENT DOCUMENTS

| | | |
|---|---|---|
| 0084325 | 7/1983 | European Pat. Off. . |
| 0089830 | 9/1983 | European Pat. Off. ........ 435/313 |
| 0103729 | 3/1984 | European Pat. Off. . |
| 7086288 | 5/1982 | Japan .................... 435/801 |
| 57-113883 | 7/1982 | Japan . |
| 60-057041 | 12/1985 | Japan . |

OTHER PUBLICATIONS

Mori et al., "Sunlight Supply System and Gas Exchange in Microalgal Bioreactor System" *Adv. in Space Res;* 1986 (McElroy and Shoog, eds) Pergammon, 1987.

Radmer et al., "An Analysis of the Productivity of a Continuous Algal Culture System", *Biotech & Bioeng.* 29, (1987).

Lee, Y. K., "Enclosed Bioreactors for the Mass Cultivation of Photosynthetic Microorganisms: The Future Trend"; *Tibtech,* Jul. 1986, pp. 186–189.

Mori et al., "Sunlight Supply System and Gas Exchange in Microalgal Bioreactor System", *Adv. in Space Res.* 1986 (McElroy and Shoog, eds.).

"An Introduction", TIR Systems Ltd., Jul. 1, 1985 24 pages.

*Primary Examiner*—Robert J. Warden
*Assistant Examiner*—William H. Beisner
*Attorney, Agent, or Firm*—Rothwell, Figg, Ernst & Kurz

[57] ABSTRACT

An apparatus is disclosed for the controlled production of microorganisms by photosynthesis in a closed photobioreactor. The closed photobioreactor contain a photosynthetic culture in a substantially sealed environment and provides a system for recirculating the reactant gas through the culture. This closed loop system can be operated with expensive carbon isotopes (i.e., $^{13}CO_2$ or $^{14}CO_2$). Also, a system is provided for removing the molecular oxygen produced in the photosynthesis reaction from the closed photobioreactor. Furthermore, a pH-regulated control valve is utilized for controlling the addition of reactant gas to the culture in response to the alkalization of the culture.

23 Claims, 4 Drawing Sheets

CLOSED PHOTOBIOREACTOR AND METHOD OF USE

BACKGROUND OF THE INVENTION

1. Field of the Invention

The present invention is directed to the controlled production of microorganisms by photosynthesis in a closed photobioreactor containing a photosynthetic culture in a substantially sealed environment and wherein a reactant gas is recirculated through the algal culture.

2. Description of the Prior Art

Algae have been cultivated artificially for such diverse purposes as the production of food for animals and humans, the treatment of sewage and waste waters, and the accumulation of radioactive wastes. More recently, algal cultures have been used for the production of enzymes having industrial and research applications and for producing oils and other materials having nutritional value. Modern biotechnology offers an opportunity for the genetic modification of algae to yield cultures capable of producing a wide variety of useful materials.

Various methods and equipment have been employed for the artificial culturing of algae. Perhaps the simplest procedures have involved the use of shallow open ponds exposed to sunlight. Such ponds are subject to contamination by dust, other microorganisms, insects and environmental pollutants and provide minimal ability to control the degree of exposure to light, temperature, respiration and other important factors. A more sophisticated approach has involved growing algal cultures in plastic-covered trenches and ponds, optionally having electrically powered pumps and agitators. These configurations reduce the chances of contamination of the culture and permit more accurate control of temperature, respiration and other parameters.

Modern photobioreactor structures are constructed to optimize the photosynthetic process by providing a means for uniformly exposing the cells in the algal culture to the optimum amount of visible light. To accomplish this, prior photobioreactors have been built with sources of light, e.g., fluorescent tubes, optical rods etc., mounted in the photobioreactor, immersed in the algal culture. The light sources are positioned inside the photobioreactor taking into consideration such characteristics as the cell density and light path length.

The principal nutrient required for the algal culture in the photosynthesis process is inorganic carbon. In known photobioreactor systems, the algal cultures obtain their carbon from carbon dioxide, often bubbled through the culture medium. The carbon dioxide is often introduced in the medium through sparging tubes or other suitable means positioned near the bottom of the photobioreactors. The bubbling of the carbon dioxide often serves a dual function in that it aids in the circulation of the algal culture.

The presently known photobioreactors operate in what could be called an open-loop mode, that is, there is a free exchange of gases between the atmosphere and the interior of the photobioreactor. These photobioreactors are characterized in that they have open tops or tops which are not in sealed relation with the tank containing the algal culture. As the photosynthesis process occurs, the gases produced, oxygen being the main by-product of the biochemical transformation, are allowed to escape from the photobioreactor into the atmosphere.

Operating the photobioreactor in this open-loop mode is often satisfactory because the materials lost to the atmosphere, i.e., carbon dioxide, evaporated water comprising the liquid culture medium, are relatively inexpensive and are not environmentally harmful. In addition, oxygen produced in the photosynthesis reaction which if contained could result in overpressurization, is allowed to freely escape. However, when very expensive reactant gases such as carbon isotopes $^{13}CO_2$ or $^{14}CO_2$ are used in such systems, economically unacceptable losses result if these rare isotopes are allowed to freely escape. Furthermore, if deuterium oxide is utilized in the liquid culture medium, excessive evaporative losses of this expensive material may occur as well.

SUMMARY OF THE INVENTION

The present invention provides a novel photobioreactor system which overcomes the aforementioned problems and which provides efficient and economical operation while enabling the use of expensive reactant gases and other reactant materials in the system. In one embodiment, the novel photobioreactor system is operated in a closed loop mode wherein the reactant gas is introduced into the liquid culture medium for photosynthetically reacting with the photosynthetic culture and is recirculated through the culture in a substantially sealed environment. The closed photobioreactor system further comprises means for removing the molecular oxygen produced by the photosynthetic reaction without substantial leakage of the reactant gas.

The present invention further provides for the use of pH sensing to control the concentration of the reactant gas in the algal culture in response to the alkalization of the culture medium. This is accomplished by monitoring the pH of the culture and actuating control means to admit the reactant gas to the culture when the pH of the culture exceeds a preselected reference value.

The invention thus enables much more economically efficient operation of a photobioreactor, as the reactant gas and the other materials are used in the liquid culture medium are substantially contained within the system and thus not lost to the atmosphere. Furthermore, controlling the concentration of the reactant gas in response to the pH of the algal culture results in efficient use of the reactant gas and prevents overpressurization when used in the closed photobioreactor system.

DESCRIPTION OF THE PREFERRED EMBODIMENTS

Figure 1:
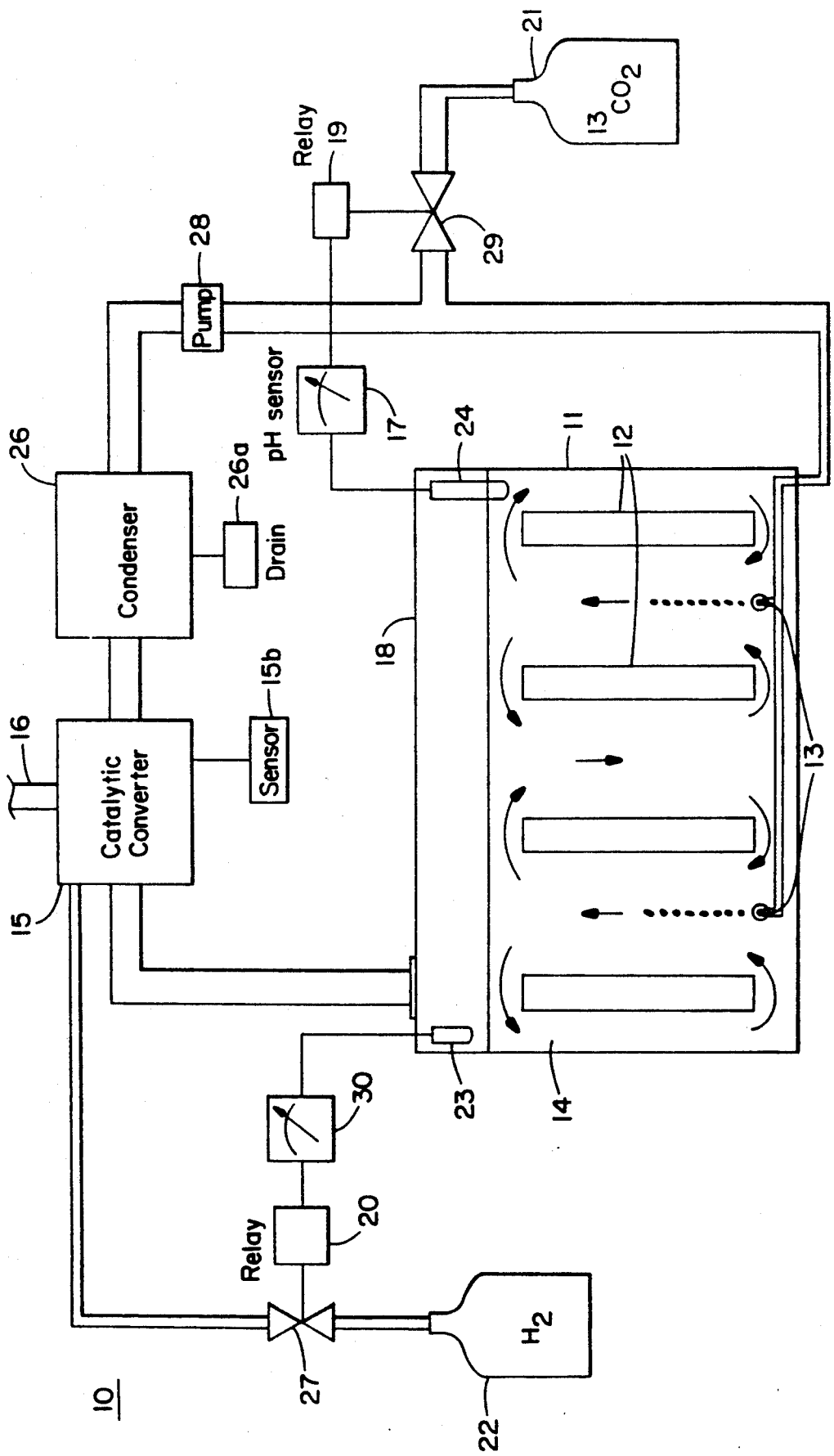
FIG. 1 is a schematic view of a closed photobioreactor system embodying the present invention.

Referring now to the drawings, FIG. 1 shows a schematic of a closed photobioreactor system 10 which includes means for removing the molecular oxygen produced in the photosynthetic reaction and means for controlling addition of the reactant gas to the photobioreactor.

As illustrated in FIG. 1, the closed photobioreactor system 10 comprises a tank 11 for containing a liquid photosynthetic culture 14 in a substantially sealed environment. The tank,s top portion 18 is constructed to be sealed with tank 11 so that gases produced in the photosynthesis reaction, e.g., molecular oxygen and any evaporation from the liquid culture, are substantially sealed within the system and prevented from being lost to the atmosphere. Light tubes 12, which can be for example fluorescent tubes, are positioned in the algal culture to provide light for the photosynthetic reaction. The light tubes can be positioned within or above the algal culture or in any way known to those skilled in the art to effect the photosynthetic reaction. For example, the light tubes 12 can be arranged in the photobioreactor as disclosed in pending U.S. patent application Ser. No. 07/163,800, assigned to assignee of the present application and incorporated herein by reference.

The reactant gas is introduced to the algal culture through sparging tubes 13, positioned near the bottom of tank 11. Bubbling the reactant gas through the liquid medium also serves to agitate and circulate the algal culture as illustrated by the arrows in $^{13}CO_2$, FIG. 1. The reactant gas, such as the isotope $CO_2$, is stored in a tank 21, and is the reactant gas used in one preferred embodiment of the present invention as shown in FIG. 1. Photosynthetically producing microorganisms using this rare carbon isotope create a universally labeled biomass which has many important uses such as in noninvasive diagnostics. For example, magnetic resonance spectroscopy can detect $^{13}C$ in sugars stored in the body and can detect organic C compounds associated with various bodily chemical functions. Other suitable reactant gases such as $^{14}CO_2$ or $CO_2$ may be utilized to fulfill the culture,s carbon requirement.

The photobioreactor system of FIG. 1 operates in a substantially sealed environment and includes means for removing the molecular oxygen produced by the photosynthesis reaction. Oxygen removal is accomplished in the embodiment shown by means of a catalytic converter 15, into which hydrogen is introduced in a controlled manner to react with the molecular oxygen in the presence of a catalyst. The water vapor formed by the combustion reaction is condensed by a condenser 26 and occupies a minimum volume in the form of water. The catalytic converter utilized in the present invention can be a basic catalytic converter in its "off the shelf" condition. Water formed in the combustion reaction may be collected and removed from the system in any known and conventional way such as through a drain 26a.

As illustrated in FIG. 1, the hydrogen introduction into catalytic converter 15 is controlled by control valve 27 which is activated by a relay 20. Control valve 27 can be solenoid valve or any valve known to those skilled in the art which can be controlled to pass a desired amount of gas. Relay 20 receives a signal responsive to oxygen concentration level from an oxygen sensor 30 and an oxygen responsive electrode 23. If oxygen electrode 23 is such that it responds to gas phase oxygen it should be positioned in the region above photosynthetic culture whereby it measures the oxygen concentration level in the gas. If oxygen electrode 23 is such that it responds to dissolved oxygen, the electrode may be submerged anywhere in the culture. Oxygen electrode 23 is electrically connected to oxygen sensor 30 which generates a signal representing the measured oxygen level. The relay 20 then opens the control valve 27 when a preset oxygen level (gas phase or liquid phase) measured by the oxygen electrode 23 is exceeded and hydrogen stored in tank 22 is caused to flow into the catalytic converter 15.

To avoid the possible introduction of an excessive amount of hydrogen into the catalytic converter, sensor and alarm means 15b can be provided to measure the hydrogen concentration flowing from the catalytic converter and to signal the presence of abnormal amounts. Ideally, hydrogen will be added at a rate sufficient to react with all of the molecular oxygen generated by photosynthesis. Excessive amounts of hydrogen could result in an explosion or the introduction of the hydrogen into the algal culture. Therefore, hydrogen addition is preferably controlled such that the combination is stoichiometrically balanced slightly on the side of excess oxygen.

As discussed above, the hydrogen is reacted with the elemental oxygen in a controlled manner and the photosynthetically generated oxygen is thereby effectively removed from the gases circulating in the tank 14. As further illustrated in FIG. 1, the gases remaining after the oxygen removal, which will comprise primarily the reactant gas, are pumped by a pump 28 back through the algal culture.

Another feature of the present invention involves the controlled addition of the reactant gas, e.g. $CO_2$, $^{13}CO_2$ or $^{14}CO_2$, to the algal culture in the closed photobioreactor. As stated above, algal cultures typically obtain their carbon from a gas, e.g. $CO_2$, which is bubbled through the algal culture medium, establishing the following equilibria:

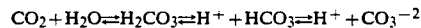

$$CO_2 + H_2O \rightleftharpoons H_2CO_3 \rightleftharpoons H^+ + HCO_3^- \rightleftharpoons H^+ + CO_3^{-2}$$

A photosynthetic algal culture will consume COz from the medium resulting in the increased alkalization of the solution. The present invention uses pH responsive means, shown in FIG. 1 in the form of a pH-regulated control valve 29, to admit the reactant gas to the algal culture responsive to the alkalization level of the culture medium. Control valve 29 is controlled by relay 19 which receives a signal indicating the pH of the algal culture from pH sensor 17 via pH electrode 24. When the measured pH value exceeds a preselected reference value, relay 19 opens the control valve 29 which admits the reactant gas to the culture from the container 21. When the pH of the medium falls below the preselected reference value, the valve is closed and the input of the reactant gas is cut off.

This aspect of the present invention has several useful applications for the culturing of photosynthetic algae; for example: (1) the system can regulate the pH of an algal culture; (2) the system can be an integral component of a closed photobioreactor in which the gas stream is recycled through the culture. Furthermore, it is important that the input of reactant gas be controlled so as not to overpressurize the photobioreactor. Adding the reactant gas only in response to the pH changes of the culture greatly alleviates the danger of overpressurization. Additionally, this system is especially useful when a closed photobioreactor is operated with expensive carbon isotopes (i.e. $^{13}CO_2$ or $^{14}CO_2$) since the isotope is only admitted to the culture in response to its consumption by the algae.

Figure 2:
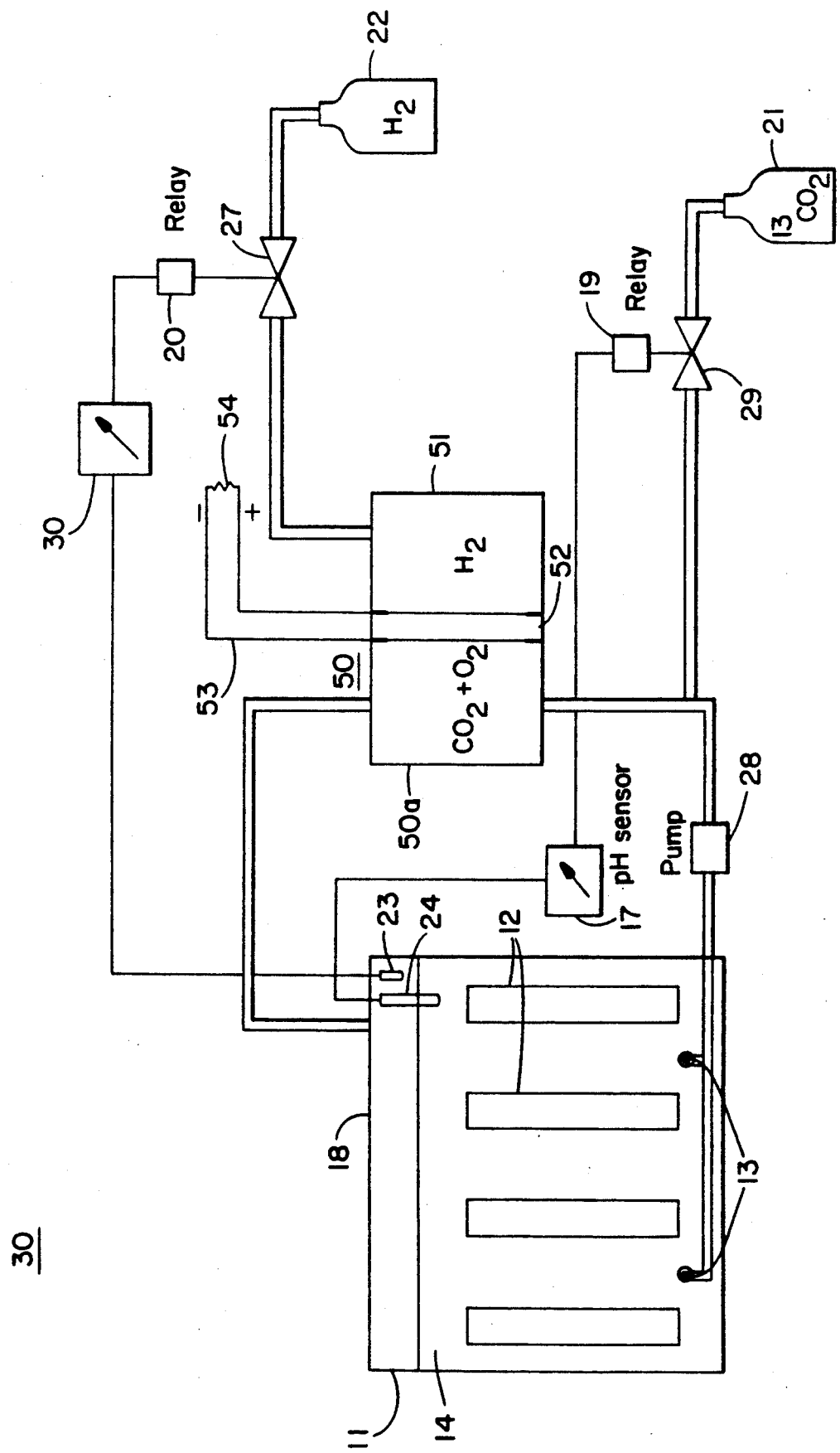
FIG. 2 is a schematic view of a closed photobioreactor system in accordance with a further embodiment of the present invention.

In an alternative embodiment of the present invention as shown in FIG. 2, molecular oxygen removal can be accomplished by a reaction means 50 for chemically reacting the molecular oxygen to form a stable chemical compound thereof with at least one additional element. In the particular embodiment shown, the reaction means 50 comprises a fuel cell 50a which causes hydrogen from a chamber 51 to react with the molecular oxygen in a controlled manner through an ion exchange membrane 52. The ion exchange membrane can be a hydrated $Al_2O_3$ membrane or any suitable membrane which facilitates ion exchange and the reaction of the hydrogen with the molecular oxygen. The fuel cell 50a illustrated is of the hydrogen-oxygen type and typically includes a catalyst, such as platinum, to assist in the reaction. Such fuel cells are well known in the art. The small amount of electrical energy produced in this reaction may be carried through wires 53 and converted to heat in resistor 54. The elements in FIG. 2 having the same reference numerals as those in FIG. 1 are the same and perform the same functions as already described in connection with FIG. 1.

As illustrated in FIG. 2, hydrogen stored in tank 22 is admitted to chamber 51 in the same controlled manner as set forth with reference to the closed photobioreactor in FIG. 1. Control valve 27 is actuated by relay 20 when the preset oxygen level measured by oxygen electrode 23 is reached. Also, when the oxygen level falls below the preset level, the hydrogen flow from tank 22 is shut off. The preset oxygen level should be at about 20%, or at about atmospheric concentration, or other desired concentration could be maintained. The oxygen removal means 50 also has means for sensing the hydrogen concentration in chamber 51 and triggers an alarm when concentration exceed preset limits. Furthermore, any membrane system which preferentially allows the diffusion of the $O_2$ over $CO_2$ could also be used.

Figure 4:
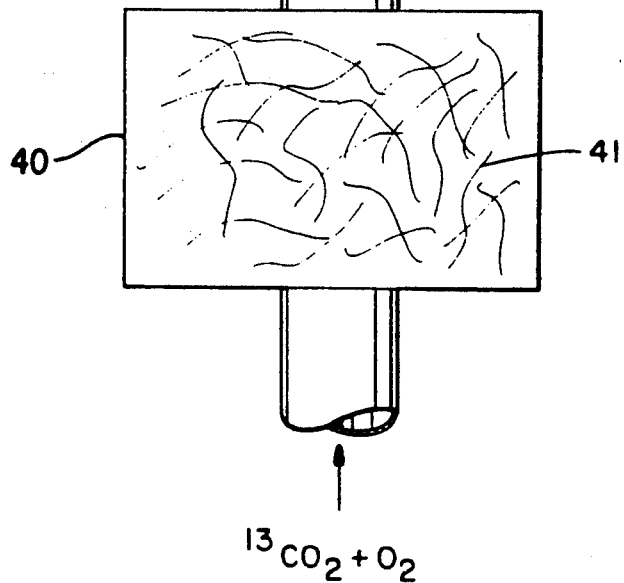
FIG. 4 illustrates a device for removing photosynthetically generated oxygen which enables the oxygen to react with metal filings.

In a further embodiment of the closed photobioreactor of the present invention, FIG. 4 illustrates the removal of photosynthetically generated oxygen from a reactant gas by enabling the oxygen to react with a metal forming a metal oxide in removal means 40. The reactant gas and the photosynthetically generated oxygen are introduced into removal means 40 containing a bed metal filings 41 (or a metal "wool") which will react with substantially all the photosynthetically generated oxygen forming a metal oxide. Oxygen is thus removed from the gas stream. Copper filings heated to approximately 500° C. can be used or any metal known to those skilled in the art which will readily form a metal oxide in the presence of oxygen.

Figure 5:
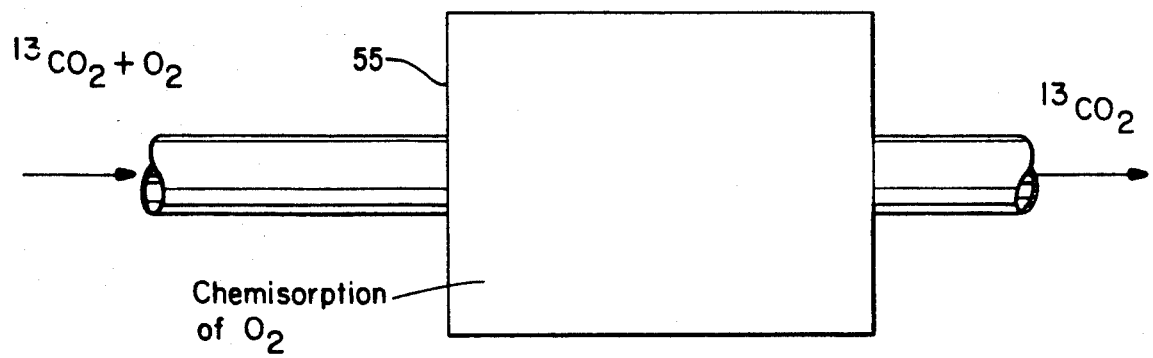
FIG. 5 illustrates the removal of photosynthetically generated oxygen by chemisorption.

In yet a further embodiment of the closed photobioreactor of the present invention, FIG. 5 illustrates the removal to photosynthetically generated oxygen by chemisorption. In chemisorption, which is a shortening of chemical absorption, the molecules stick to the surface of a metal as the result of a chemical, and usually a convalent, bond. As shown in FIG. 5, the reactant gas and the photosynthetically generated oxygen are introduced into the apparatus 55 wherein a solid active metal removes the oxygen by chemisorption. A device of this type is an Oxisorb, manufactured by Analalabs, Inc.

Figure 6:
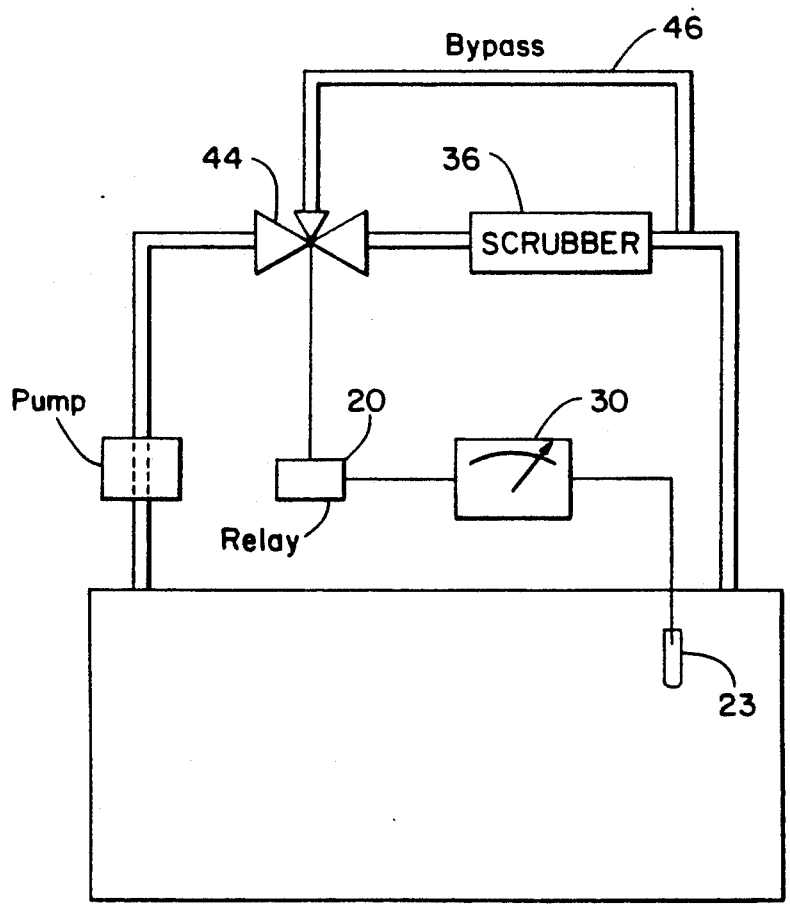
FIG. 6 shows a further embodiment of the present invention which removes photosynthetically generated oxygen from a reactant gas by an oxygen scrubber.

In still a further embodiment of the present invention, FIG. 6 illustrates removing photosynthetically generated oxygen from a reactant gas by an oxygen scrubber. Oxygen scrubber 36 utilizes a "BTS catalyst", which is first reduced with $H_2$ or CO, and placed in the gas stream to effectuate oxygen removal. Also, "Ridox" which is an active granular reagant can be used in oxygen scrubber 36 to remove the oxygen.

The closed photobioreactor shown in FIG. 6 operates in a manner substantially similar to the photobioreactor in FIG. 1. Relay 20 receives a signal responsive to the oxygen concentration level from oxygen sensor 30 and an oxygen responsive electrode 23. Relay 20 opens a control valve 44 when a preset oxygen level is exceeded thus introducing the reactant gas and photosynthetically generated oxygen into oxygen scrubber 36. When the oxygen concentration level is below the preset value, the reactant gas flows through control valve 44 and along bypass lines 46 to bypass oxygen scrubber 36. In both cases, the reactant gas is recirculated through the photosynthetic culture as discussed with reference to FIG. 1. Furthermore, additional reactant gas ($CO_2$, $^{13}CO_2$ or $^{14}CO_2$) can be supplied to the culture as shown in FIG. 1.

In addition to the solid oxygen scrubbers described above, a liquid scrubber can be used in scrubber 36 as well to remove the photosynthetically generated oxygen from the reactant gas. In this embodiment, the gas stream is bubbled through a liquid containing chemicals which react with oxygen, and thus effectively removing it from the gas stream. In a preferred embodiment, this liquid comprises 0.4M Cr ($ClO_4$) in HCl with amalgamated Zn, but any such liquid known to those skilled in the art could be used as well.

Figure 3:
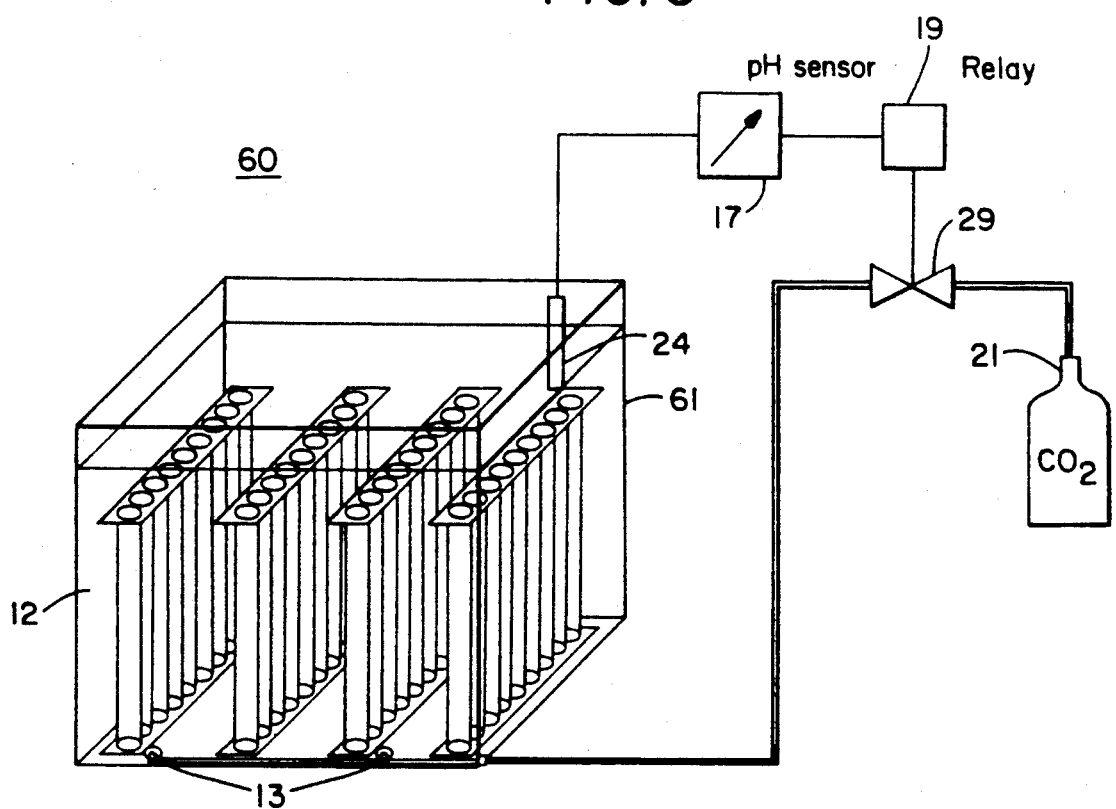
FIG. 3 is a perspective view of an open photobioreactor in accordance with a further embodiment of the present invention.

In a further embodiment of the present invention, FIG. 3 illustrates the pH controlled addition of reactant gas such as carbon dioxide into the algal culture in an open photobioreactor 60. The control valve 29 controls the introduction of $CO_2$ to the algal culture in response to the culture's alkalization in substantially the same way as described with reference to FIG. 1. Here, however, the reactor container is formed of a tank 61 which is open to the atmosphere and the inexpensive gases are allowed to freely escape. The pH-controlled addition of reactant gas to the algal culture is advantageous because the system can regulate the pH of the culture, and the reactant gas is efficiently used when admitted on as required to satisfy the reaction rate within the culture in response to its consumption by algae.

While it is apparent that the preferred embodiment shown and described provides certain advantages, it should be understood that such embodiments are presented for the purpose of making a full, clear and detailed disclosure thereof and that many of the advantages of the present invention can nevertheless be realized in other configurations, and it will be appreciated that various modifications, changes and adaptions can be made, all of which are intended to be comprehended within the scope of the appended claims.

We claim:

1. A closed photobioreactor comprising:
    (a) container means for containing a photosynthetic algal culture in a substantially sealed environment;
    (b) means for introducing light into said container means;
    (c) means for introducing a reactant gas into said container means for photosynthetically reacting with a culture in said container means in the presence of light such that molecular oxygen is produced as a by-product, the molecular oxygen and unconsumed reactant gas forming a gas mixture;

(d) means for removing the molecular oxygen from the gas mixture without leaving by-products of the oxygen removal to be recirculated and without substantial leakage of the unconsumed reactant gas;

(e) means for recirculating the unconsumed reactant gas after oxygen removal through an algal culture in the substantially sealed environment when the reactant gas and the algal culture are present in said container means; and wherein said means for removing molecular oxygen comprises means for enabling a combustion reaction with the oxygen and at least one other element to form a stable chemical compound thereof with said at least one other element.

2. The closed photobioreactor as set forth in claim 1 further comprising means for sensing the concentration level of oxygen in said container means.

3. The closed photobioreactor as set forth in claim 2 wherein said means for removing molecular oxygen comprises a first chamber for containing the molecular oxygen, a second chamber for containing hydrogen and an ion exchange membrane separating said first and second chambers for enabling the hydrogen when present in said second chamber to react with the oxygen.

4. The closed photobioreactor as set forth in claim 3 wherein the ion exchange member is made of $Al_2O_3$.

5. The closed photobioreactor as set forth in claim 3 further comprising means for introducing the hydrogen into said second chamber.

6. The closed photobioreactor as set forth in claim 1 wherein said means for enabling a combustion reaction comprises a catalytic converter.

7. The closed photobioreactor as set forth in claim 6 further comprising means for introducing hydrogen into said catalytic converter.

8. The closed photobioreactor as set forth in either claim 5 or claim 7 wherien said means for introducing the hydrogen comprises valve means actuated responsive to said means for sensing the concentration level of oxygen.

9. The closed photobioreactor as set forth in claim 1 further comprising means for controlling the addition of said reactant gas into said culture in response to the pH of said culture.

10. The closed photobioreactor as set forth in claim 9 wherein said means for controlling the addition of said reactant gas comprises pH-controlled valve means for admitting said reactant gas responsive to the pH of the algal culture exceeding a predetermined level.

11. The closed photobioreactor as set forth in claim 1 wherein said means for introducing reactant gas is a means for introducing carbon dioxide.

12. The closed photobioreactor as set forth in claim 1 wherein means for introducing a reactang gas is a means for introducing $^{13}Co_2$ or $^{14}CO_2$.

13. A method of performing a continuous photosynthetic reaction process comprising:

(a) maintaining a photosynthetic algal culture in a substantially sealed environment;

(b) circulating a reactant gas through said culture in the presence of light and photosynthetically reacting said gas with said culture and thereby producing molecular oxygen in said reactant gas as a by-product, the molecular oxygen and unconsumed reactant gas forming a gas mixture;

(c) removing the molecular oxygen produced after photosynthetically reacting the reactant gas with said culture, from the gas mixture, said removing the molecular oxygen comprising chemically reacting said oxygen with at least one additional element to form a stable chemical compound therewith and without the stable chemical compound or other by-product the chemical reaction being recirculated into said algal culture and wherein said removing said molecular oxygen comprises introducing said molecular oxygen into a first chamber, introducing hydrogen into a second chamber and reacting said molecular oxygen with said hydrogen through an ion exchange membrane separating said first and second chambers to form water as at least one by-product; and (d) recirculating the unconsumed reactant gas after oxygen removal into said algal culture in said substantially sealed environment.

14. The method of performing a continuous photosynthetic reaction process as set forth in claim 13, further comprising the step of controlling the introduction of hydrogen into said second chamber.

15. The method of performing a continuous photosynthetic reaction process as set forth in claim 14 further comprising sensing the level of oxygen concentration in said reactant gas.

16. The method of performing a continuous photosynthetic reaction process as set forth in claim 13 wherein introducing a reactant gas into said algal culture comprises introducing $Co_2$ or $^{13}CO_2$ or $^{14}CO_2$.

17. A method of performing a continuous photosynthetic reaction process comprising:

(a) maintaining a photosynthetic algal culture in a substantially sealed environment;

(b) circulating a reactant gas through said culture in the presence of light and photosynthetically reacting said gas with said culture and thereby producing molecular oxygen in said reactant gas as a by-product, the molecular oxygen and unconsumed reactant gas forming a gas mixture;

(c) removing the molecular oxygen produced after photosynthetically reacting the reactant gas with said culture, from the gas mixture, said removing the molecular oxygen comprising enabling a combustion reaction with the molecular oxygen and at least one other element to form a stable chemical compound thereof with at least one other element, and without the stable chemical compound or other by-product of the chemical reaction being recirculated into said algal culture; and (d) recirculating the unconsumed reactant gas after oxygen removal into said algal culture in said substantially sealed environment.

18. The method of performing a continuous photosynthetic reaction process as set forth in claim 17 wherein said removing said molecular oxygen comprises reacting said molecular oxygen with hydrogen in a catalytic converter to form water as at least one by-product.

19. The method of performing a continuous photosynthetic reaction process as set forth in claim 18 further comprising the step of controlling the introduction of hydrogen into said catalytic converter.

20. The method of performing a continuous photosynthetic reaction process as set forth in claim 19 further comprising sensing the level of oxygen concentration in said reactant gas.

21. The method of performing a continuous photosynthetic reaction process as set forth in claim 15 or claim 20 wherein said step of controlling the addition of hydrogen comprises actuating a valve means responsive to said sensing the level of oxygen concentration when a preset level of oxygen concentration is exceeded.

22. A closed photobioreactor comprising:
    (a) container means for containing a photosynthetic algal culture in a substantially sealed environment;
    (b) means for introducing light into said container means;
    (c) means for introducing a reactant gas into said container means for photosynthetically reacting with culture in said container means in the presence of light such that molecular oxygen is produced as a by-product, the molecular oxygen and unconsumed reactant gas forming a gas mixture;
    (d) means for removing the molecular oxygen from the gas mixture without leaving by-products of the oxygen removal to be recirculated and without substantial leakage of the unconsumed reactant gas;
    (e) means for recirculating the unconsumed reactant gas after oxygen removal through an algal culture in the substantially sealed environment; and
    wherein said means for removing molecular oxygen comprises means for enabling the molecular oxygen to react with hydrogen through an ion exchange membrane.

23. The closed photobioreactor as set forth in claim 22, wherein said means for enabling comprises a first chamber for containing the molecular oxygen, a second chamber for containing hydrogen and an ion exchange membrane separating said first and second chambers for enabling the hydrogen when present in said second chamber to react with said oxygen.

* * * * *